(12) United States Patent  
Tebano et al.

(10) Patent No.: US 8,626,454 B2  
(45) Date of Patent: Jan. 7, 2014

(54) METHOD AND SYSTEM FOR DETERMINING THE POTENTIAL FRICTION BETWEEN A TYRE FOR VEHICLES AND A ROLLING SURFACE

(75) Inventors: Riccardo Tebano, Milan (IT); Glorgio Audisio, Milan (IT)

(73) Assignee: Pirelli Tyre S.p.A., Milan (IT)

( * ) Notice: Subject to any disclaimer, the term of this patent is extended or adjusted under 35 U.S.C. 154(b) by 0 days.

(21) Appl. No.: 13/825,712

(22) PCT Filed: Sep. 28, 2011

(86) PCT No.: PCT/IB2011/002313  
§ 371 (c)(1),  
(2), (4) Date: Apr. 17, 2013

(87) PCT Pub. No.: WO2012/042369  
PCT Pub. Date: Apr. 5, 2012

(65) Prior Publication Data  
US 2013/0211741 A1  Aug. 15, 2013

Related U.S. Application Data

(60) Provisional application No. 61/388,797, filed on Oct. 1, 2010.

(30) Foreign Application Priority Data

Sep. 30, 2010  (IT) .............................. MI2010A1789

(51) Int. Cl.  
*G01N 19/02* (2006.01)  
*G01L 5/00* (2006.01)  
*G06F 19/00* (2011.01)  
*G06F 17/40* (2006.01)

(52) U.S. Cl.  
USPC .......... 702/41; 73/9; 73/146; 702/1; 702/127; 702/187; 702/189

(58) Field of Classification Search  
USPC .......... 73/9, 146, 432.1, 865.8; 701/1, 51, 65, 701/70, 71, 73, 82; 702/1, 33, 41, 42, 43, 702/127, 182, 187, 189; 708/100, 105, 200  
IPC .................. B60B 2900/00,2900/10, 2900/121, B60B 2900/1212; B60C 23/00, 23/06, 23/063, B60C 23/064, 23/065, 23/066, 99/00; B60T 2240/00; G01D 21/00; G01L 1/00, 5/00; G01N 5/00, 19/00, 19/02; G01P 15/00, 2015/00; G06F 11/00, 11/30, 11/32, 17/00, 17/40, 19/00  
See application file for complete search history.

(56) References Cited

U.S. PATENT DOCUMENTS

| | | | | |
|---|---|---|---|---|
| 3,301,039 A * | 1/1967 | Kummer | | 73/9 |
| 3,500,681 A * | 3/1970 | Shively | | 73/146 |
| 4,662,211 A * | 5/1987 | Strong | | 73/9 |
| 4,958,512 A * | 9/1990 | Johnsen | | 73/9 |
| 6,226,587 B1 * | 5/2001 | Tachihata et al. | | 701/72 |
| 6,538,566 B1 | 3/2003 | Morand et al. | | |
| 6,550,320 B1 * | 4/2003 | Giustino | | 73/146 |
| 6,561,018 B2 * | 5/2003 | Mancosu et al. | | 73/146 |
| 7,404,318 B2 * | 7/2008 | Merino-Lopez et al. | | 73/146 |
| 7,546,764 B2 * | 6/2009 | Morinaga et al. | | 73/146 |
| 7,680,577 B2 * | 3/2010 | Mori | | 701/70 |
| 7,918,131 B2 * | 4/2011 | Matsuda et al. | | 73/146.5 |
| 2002/0166373 A1 * | 11/2002 | Mancosu et al. | | 73/146 |
| 2003/0062994 A1 * | 4/2003 | Morand et al. | | 340/443 |
| 2003/0164036 A1 * | 9/2003 | Giustino | | 73/146 |
| 2006/0041365 A1 * | 2/2006 | Mori | | 701/70 |
| 2007/0205879 A1 | 9/2007 | Matsuda et al. | | |
| 2007/0240502 A1 * | 10/2007 | Morinaga et al. | | 73/146 |
| 2008/0015763 A1 | 1/2008 | Kitazaki et al. | | |
| 2008/0016955 A1 * | 1/2008 | Merino-Lopez et al. | | 73/146 |
| 2009/0105921 A1 | 4/2009 | Hanatsuka et al. | | |
| 2010/0131208 A1 | 5/2010 | Mancosu et al. | | |
| 2011/0257902 A1 | 10/2011 | Melzi et al. | | |

FOREIGN PATENT DOCUMENTS

| | | |
|---|---|---|
| EP | 1 813 493 A1 | 8/2007 |
| EP | 1 878 596 A2 | 1/2008 |
| EP | 1 897 706 A1 | 3/2008 |
| WO | WO 2008/065465 A1 | 6/2008 |
| WO | WO 2010/073272 A1 | 7/2010 |

OTHER PUBLICATIONS

International Search Report from the European Patent Office for International Application No. PCT/IB2011/002313, mailing date Dec. 6, 2011.

Breuer, B. et al., "Methods and Instruments for On-Board Measurement of Tyre/Road Friction," SAE Conference, Dearborn, USA, 942470 (1994).

Eichhorn, U. et al., "Prediction and monitoring of tyre/road friction," Proc. FISITA 24$^{th}$ Congress: Safety, the Vehicle and the Road Tech. Papers, London, UK, Part 2, pp. 67-74, (1992).

* cited by examiner

*Primary Examiner* — Edward Cosimano

(74) *Attorney, Agent, or Firm* — Finnegan, Henderson, Farabow, Garrett & Dunner, L.L.P.

(57) ABSTRACT

A method and system for determining the potential friction between a tire and a rolling surface wherein: the tire is rotated on the rolling surface so as to subject a crown portion of the tire to an acceleration radial component; data are obtained which are representative of the acceleration radial component to which the crown portion is subjected during at least one tire revolution; starting from the data, data are selected which are representative of at least one transition region of the acceleration radial component; the selected data are processed so as to obtain information correlated with the steepness of transition of the at least one transition region; and the potential friction is estimated on the basis of the information correlated with the steepness of transition.

10 Claims, 7 Drawing Sheets

METHOD AND SYSTEM FOR DETERMINING THE POTENTIAL FRICTION BETWEEN A TYRE FOR VEHICLES AND A ROLLING SURFACE

CROSS REFERENCE TO RELATED APPLICATIONS

This application is a national phase application based on PCT/IB2011/002313, filed Sep. 28, 2011, which claims the benefit of priority of Italian Patent Application No. MI2010A001789, flied Sep. 30, 2010, and the benefit of U.S. Provisional Application No. 61/388,797, filed Oct. 1, 2010, the content of all of which is incorporated herein by reference.

BACKGROUND OF THE INVENTION

1. Field of the Invention

The invention relates to a method and system for determining the potential friction between a tyre for vehicles and a rolling surface.

2. Description of the Related Art

The incorporation of electronic devices inside the tyres is becoming increasingly important in order to increase the vehicle safety. Such devices may, for example, include sensors and other components suitable for obtaining information about various quantities of a tyre such as, temperature, pressure, acceleration, number of tyre revolutions, vehicle speed. Such devices may further include a transmitter (typically wireless) for sending out of the tyre (typically to a control unit on board of the vehicle) the information obtained by the sensors and a microprocessor suitable for gathering and processing signals coming from the sensors, prior to the transmission thereof. Optionally, such devices may also include a receiver (typically wireless) for receiving any information from the outside (for example, from a control unit on board of the vehicle).

In this context, analysing and monitoring the interaction between the tyres of a vehicle and the rolling surface whereon the same operate during the use thereof may provide useful information to the driver of a vehicle as a driving aid and/or provide useful information to automatic control systems the same vehicle may be provided with and/or provide useful information to other vehicles or infrastructures other than the vehicle itself in order to enable, for example, traffic control and monitoring systems. For example, such information may be used by a traffic control and monitoring system for providing warning signals and/or adjusting the speed limits in adaptive speed limit systems.

In particular, the estimate of the potential friction may be important for allowing the development of technologies for active control systems of a vehicle dynamics or for driver assistance systems (Advanced Driver Assistance Systems, or ADAS).

The potential friction is defined as the ordinate of the absolute maximum point in a kinetic friction/slip curve. The kinetic friction is defined as the ratio between the force exchanged in the plane of contact between the tyre and the rolling surface and the vertical load acting on the tyre.

FIG. 1 shows two exemplary patterns of the kinetic friction coefficient $\mu_k$ as a function of the slip $\sigma$ for two different conditions of tyre-rolling surface system.

When the conditions of the tyre-rolling surface system vary, that is, the operating conditions of the tyre (such as vertical load acting on the tyre, tyre inflation pressure, speed, wear, temperature, etc.), the features of the tyre itself (structure, mixture, etc.), and/or the features and conditions of the rolling surface (presence of slippery elements such as snow, ice, leaves, roughness, etc.), the relationship between slip and kinetic friction is described by a different curve ($\mu pot1$, $\mu pot2$) and the potential friction $\mu pot$ is correspondingly different.

In the practice, the potential friction fixes a limit condition beyond which the tyre grip conditions begin to degrade up to reaching an asymptotic condition in which, even with increasing slip, the friction coefficient remains substantially constant and lower than the maximum friction (i.e. than the potential friction itself).

Systems capable of estimating the potential friction in a tyre-rolling surface system are known in the art such as, for example, the same Bracking Antilock Systems (ABS). Such systems, however, determine the potential friction in braking conditions, when the forces exchanged at the tyre-rolling surface interface are close to the maximum value, that is, at high slips.

The Applicant is instead directing its development activities towards systems capable of determining the potential friction in a tyre-rolling surface system under conditions of "free rolling" or "steady state" of the system, that is, under stationary rolling conditions (for example, at a constant speed, substantially in the absence of braking and steering).

However, considering that the condition of "free rolling" or "steady state" corresponds to small slip values (e.g. less than 1%) and that the friction/slip curves relating to different conditions of the tyre-rolling surface system (which correspond to different potential frictions) are concentrated in the proximity of the origin, almost overlapped (see the region highlighted in FIG. 1), the determination of the potential friction in conditions of "free rolling" is extremely difficult.

The international patent application no. WO 2010/073272 in the name of the same Applicant describes a technique for determining the potential friction without the need of achieving high slips.

Bert Breuer et al. ("Methods and Instruments for On-Board Measurement of Tyre/Road Friction", SAE Conference, Dearborn. USA 1994) and U. Eichhorn et al. ("Prediction and monitoring of tyre/road friction", in Proc. FISITA 24th Congress: Safety, the Vehicle and the Road Tech. Paper, London, UK, 1992, vol. 2, pp. 67-74) describe a technique for determining the friction between a tyre and the road from the deformation of elements of the tyre tread.

In the development of systems capable of determining the potential friction in a tyre-rolling surface system under conditions of "free rolling" or "steady state" of the system, the Applicant has carried out activities of acquisition and analysis of curves related to the longitudinal and lateral acceleration component measured, revolution after revolution, by an accelerometer placed on the inner liner of a tyre. This based on the observation that friction is a force that opposes the relative motion between tyre and rolling surface along the longitudinal and lateral direction of the tyre.

SUMMARY OF THE INVENTION

During these activities of acquisition and analysis, having also available curves related to the acceleration radial component measured, revolution after revolution, by an accelerometer placed on the inner liner of a tyre, the Applicant has accidentally observed that two curves of acceleration radial component obtained with two different rolling surfaces (dry asphalt and wet granite) exhibited differences at a very circumscribed transition region wherein—due to the exit of the accelerometer from the footprint of the tyre—the acceleration radial component passed from a nearly zero value to a maximum value thereof.

Starting from such totally accidental initial observation (afterwards verified also by analysing curves obtained by rolling on different surfaces), the Applicant has surprisingly found that the steepness of transition of the curves of the acceleration radial component, at two transition regions at the entry and exit from the footprint, depends on the interaction between the tyre and the rolling surface.

The Applicant has further found that the aforementioned steepness of transition may be correlated with the potential friction.

In particular, the Applicant has found that at said transition regions, the steepness of transition is even higher, the lower the potential friction between the tyre and the rolling surface.

In a first aspect thereof, the present invention relates to a method for determining the potential friction between a tyre and a rolling surface, a footprint being defined between said tyre and said rolling surface, said method comprising:

rotating the tyre on the rolling surface so as to subject a crown portion of the tyre to an acceleration radial component, according to a radial direction of the tyre;

obtaining data representative of the acceleration radial component to which said crown portion is subjected during at least one tyre revolution, said acceleration radial component comprising two regions $R_{drop}$ and a region $R_{in}$, in which said regions $R_{drop}$ represent two regions in which, due to the entry and exit of said crown portion into/from the footprint, the acceleration radial component respectively undergoes, in absolute value, an abrupt drop from a maximum value to a value about zero and an abrupt increase from a value about zero to a maximum value, and said region $R_{in}$ represents a region in which, due to the passage of said crown portion within the tyre footprint, the acceleration radial component is about zero;

starting from said data, selecting data representative of at least one transition region of said acceleration radial component, said at least one transition region comprising at least one portion of one of said regions $R_{drop}$, contiguous to said region $R_{in}$;

processing the selected data so as to obtain information correlated with the steepness of transition of said at least one transition region; and estimating the potential friction on the basis of said information correlated with the steepness of transition.

In a second aspect thereof, the present invention also relates to a system for determining the potential friction between a tyre and a rolling surface, a footprint being defined between said tyre and said rolling surface, said system comprising at least one processing unit adapted to:

obtain data representative of the acceleration radial component to which said crown portion is subjected during at least one tyre revolution, said acceleration radial component comprising two regions $R_{drop}$ and a region $R_{in}$, in which said regions $R_{drop}$ represent two regions in which, due to the entry and exit of said crown portion into/from the footprint, the acceleration radial component respectively undergoes, in absolute value, an abrupt drop from a maximum value to a value about zero and an abrupt increase from a value about zero to a maximum value, and said region $R_{in}$ represents a region in which, due to the passage of said crown portion within the tyre footprint, the acceleration radial component is about zero;

starting from said data, select data representative of at least one transition region of said acceleration radial component, said at least one transition region comprising at least one portion of one of said regions $R_{drop}$, contiguous to said region $R_{in}$;

process the selected data so as to obtain information correlated with the steepness of transition of said at least one transition region and estimate the potential friction on the basis of said information correlated with the steepness of transition.

In the present description and following claims:

the expression "free rolling" is used to indicate a stationary rolling condition of the tyre, such as for example at nearly constant speed, in the substantial absence of braking and steering;

the expression "crown portion" of a tyre is used to indicate a portion of the tyre that extends between the sides of the same according to a lateral direction of the tyre;

the terms "lateral" and "laterally" are used to indicate quantities measured in a direction parallel to the axis of rotation of the tyre;

the terms "radial" and "radially" are used to indicate quantities measured in the direction perpendicular to the axis of rotation of the tyre;

the terms "longitudinal" and "longitudinally" are used to indicate quantities measured tangentially to the tyre and perpendicularly to the lateral direction and to the radial direction.

The present invention, in at least one of the above aspects thereof, can exhibit at least one of the following preferred features.

In one embodiment, said at least one transition region also comprises at least one portion of $R_{in}$ contiguous to said at least one portion of region $R_{drop}$.

Preferably, the selected data are representative of the transition region at the exit of said crown portion from the footprint of the tyre. In particular, said at least one portion of region $R_{drop}$, which is comprised in said at least one transition region, is a portion of the region $R_{drop}$ in which—due to the exit of the crown portion from the footprint—the acceleration radial component undergoes, in absolute value, an abrupt increase from a value about zero to a maximum value. The Applicant has, in fact, verified that the difference in the transition steepness between two curves of the acceleration radial component corresponding to two different tyre-rolling surface systems, (and, therefore, to two different potential values of friction) is more visible in the transition region at the exit from the footprint than in the transition region at the entrance into the footprint.

In one embodiment, data are selected which are also representative of another transition region which comprises at least one portion of the other of said two regions $R_{drop}$, contiguous to said region $R_{in}$.

In one embodiment, the tyre is rotated under conditions of free rolling.

Advantageously, the data representative of the acceleration radial component are obtained at each tyre revolution.

In a preferred embodiment, prior to obtaining the information correlated with the steepness of transition of said at least one transition region, the selected data are processed through a normalization procedure. Preferably, according to the normalization procedure, the data value is divided by at least one reference value corresponding to the (average) value of the acceleration radial component in a region $R_{out}$, the region $R_{out}$ representing a region away from the footprint of the tyre, wherein the value of the acceleration radial component is about equal to the centrifugal acceleration of the tyre. As shown in more detail below, the Applicant has found, in fact, that such a normalization procedure allows making the estimate of the potential friction almost independent of the angular velocity of the tyre.

Advantageously, the estimate of the potential friction is made at each revolution of the tyre. Alternatively, an average may be performed on a certain number of revolutions of tyre (e.g. five revolutions maximum in order to make real time estimates).

Advantageously, the processing is carried out starting from data representative of at least 5 points of said at least one transition region. Preferably, the processing is carried out from data representative of at least 8 points of said at least one transition region; even more preferably, the processing is carried out from data representative of at least 10 points of said at least one transition region.

In one embodiment, the information correlated with the steepness of transition of said at least one transition region comprises the value of at least one transition steepness parameter, said parameter being a parameter of a parametric function adapted to approximate the data representative of said at least one transition region and being indicative of the steepness of transition of said at least one transition region. Advantageously, the value of said at least one transition steepness parameter is obtained by determining the value of said parameter that allows the parametric function to best approximate said data representative of said at least one transition region.

In another embodiment, the information correlated with the steepness of transition of said at least one transition region comprises a curve representative of a value or class of known potential friction values. Said curve representative of a value or class of known potential friction values is advantageously obtained by identifying, among a plurality of pre-stored reference curves corresponding to values or classes of known potential friction values, a curve that best approximates said data representative of said at least one transition region.

Advantageously, the system also comprises a monitoring device operatively associated with the tyre, said monitoring device comprising an accelerometer, operatively associated with said crown portion, suitable for measuring the acceleration radial component to which said crown portion is subjected during the rolling of the tyre.

Advantageously, said at least one processing unit is operatively connected to said monitoring device so as to receive a signal representative of the acceleration radial component measured by the accelerometer or data representative of said signal.

BRIEF DESCRIPTION OF THE DRAWINGS

Further features and advantages of the present invention will become clear from the following detailed description of some exemplary embodiments thereof, given by way of non-limiting example only, a description that shall be made with reference to the attached drawings, wherein.

DETAILED DESCRIPTION OF THE INVENTION

Figure 1:
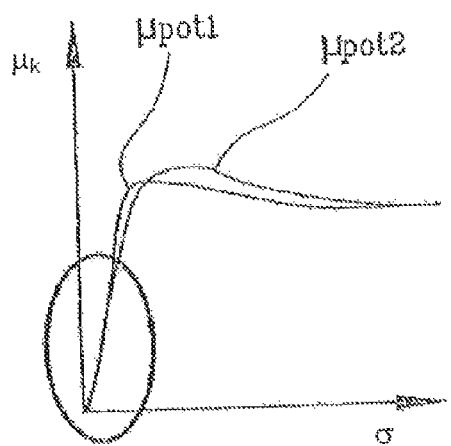
FIG. 1 schematically shows two examples of friction/slip curves relating to two different conditions of interaction between tyre and rolling surface, corresponding to two different values of potential friction.
Figure 2:
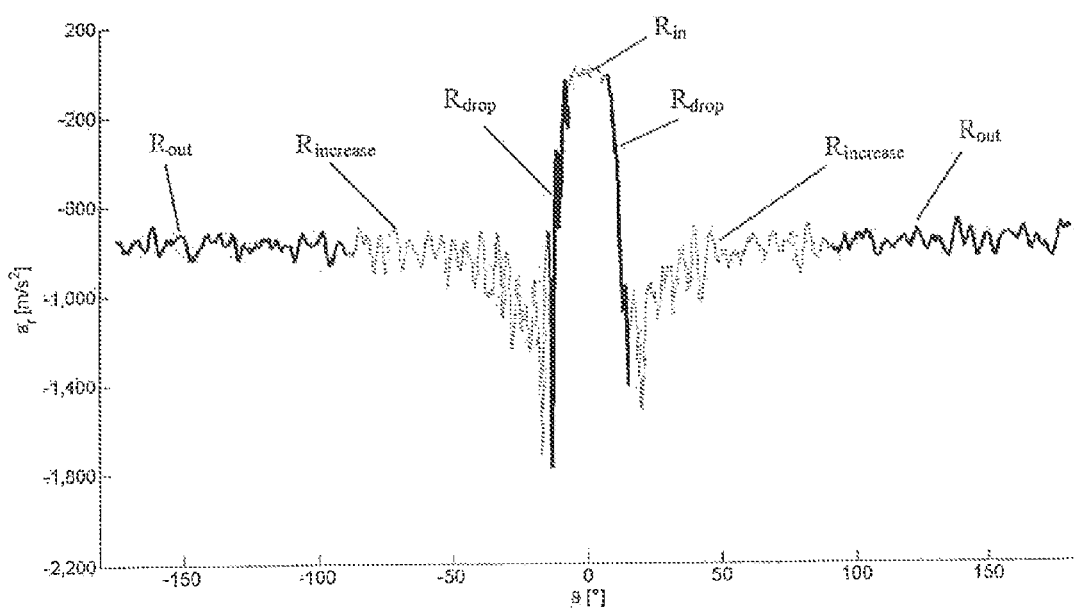
FIG. 2 shows a curve representative of the acceleration radial component measured during a revolution of the tyre by an accelerometer mounted at the centre of an inner liner of a tyre as a function of the angular position of the accelerometer relative to the centre of the footprint.

FIG. 2 shows an example of acceleration radial component measured during one revolution of the tyre, by an accelerometer mounted at the centre of the inner liner of a tyre as a function of the angular position of the accelerometer relative to the centre of the footprint ($\theta=0$ indicates an angular position of the accelerometer at the centre of the footprint, $\theta>0$ indicates angular positions after the centre of the footprint, $\theta<0$ indicates the angular positions before the centre of the footprint, $\theta=\pm 180°$ indicates an angular position of the accelerometer diametrically opposite the centre of the footprint).

The curve refers to a tyre, or more specifically a PIRELLI P6 CINTURATO™ 205/55 tyre, mounted on the front right wheel of a FIAT STILO™ automobile travelling in a straight line at a speed of 60 km/h on dry asphalt.

The acceleration radial component measured by the accelerometer is approximately given by the following formula, except for small contributions such as the gravitational one:

$$a_r = \frac{d^2 r}{dt^2} + \omega^2 r$$

where r is the distance of the trajectory followed by the accelerometer during the rolling of the tyre from the centre of the tyre (which, outside the footprint, approximately corresponds to the radius $r_0$ of the tyre) and $\omega$ is the angular speed of the accelerometer relative to the trajectory (which, outside the footprint, approximately corresponds to the angular speed $\omega_0$ of the tyre).

In such curve, 4 main regions may be identified:

1. the first region, hereinafter referred to as $R_{out}$, is the situation in which the accelerometer is located away from the footprint of the tyre. In this region, the acceleration radial component measured by the accelerometer is substantially equal to the centrifugal acceleration $\omega^2_0 r_0$ of the tyre. For example, in the case of FIG. 2, this region may correspond to:

$R_{out} \approx \{\theta \in (-180°, -90°) \cup (90°, 180°)\}$ 2. the second region, hereinafter referred to as $R_{increase}$, represents either the situation in which the accelerometer is approaching the tyre footprint and, due to the deformation undergone by the surface on which the accelerometer is positioned, the acceleration radial component increases in absolute value going from a value equal to that taken in $R_{out}$ to a maximum value, or the situation in which the accelerometer is moving away from the tyre footprint and, due to the deformation undergone by the surface on which the accelerometer is positioned, the acceleration radial component decreases in absolute value going from a maximum value to a value equal to that taken in $R_{out}$. For example, in the case of FIG. 2, this region may correspond to:

$$R_{increase} \approx \{\theta \in (-90°, -15°) \cup (15°, 90°)\}$$

3. the third region, hereinafter referred to as $R_{drop}$, is the situation where, due to entry into (exit from) the footprint, the acceleration radial component detected by the accelerometer undergoes, in absolute value, an abrupt decrease (or abrupt increase), going from a maximum value to nearly zero (or from a nearly zero value to a maximum value). For example, in the case of FIG. 2, this region may correspond to:

$$R_{drop} \approx \{\theta \in (-15°, -10°) \cup (10°, 15°)\} \quad (3)$$

4. the fourth region, hereinafter referred to as $R_{in}$, is the situation in which the accelerometer is passing along the footprint of the tyre and detects a nearly zero acceleration radial component (during the transition in the footprint, the accelerometer moves, in fact, according to an almost rectilinear motion and not rotatory anymore, so ω is substantially equal to 0), for example less than 30 g, preferably less than 10 g, where g is the acceleration of gravity. For example, in the case of FIG. 2, this region may correspond to:

$$R_{in} \approx \{\theta \in (-10°, 10°)\} \quad (4)$$

The extension of the four areas mentioned above may depend, in general, on a series of parameters, such as for example the tyre structure, the tyre inflation pressure, the vertical load acting on the tyre and/or the speed.

For the purposes of the invention, the term "transition region" is used to indicate a region of a curve of acceleration radial component corresponding to a region $R_{drop}$, optionally combined with at least one portion of $R_{in}$ contiguous to such region $R_{drop}$, or with a portion of region $R_{drop}$ contiguous to $R_{in}$, optionally combined with at least one portion of $R_{in}$ contiguous to such region $R_{drop}$.

The Applicant has found that the shape, and in particular, the steepness of the transition of the two transition regions of a curve of the acceleration radial component are correlated with the potential friction.

In particular, the Applicant has found that the steepness of transition of the curve of the acceleration radial component at the two transition regions is even higher, the lower the potential friction between the tyre and the rolling surface.

Figure 3:
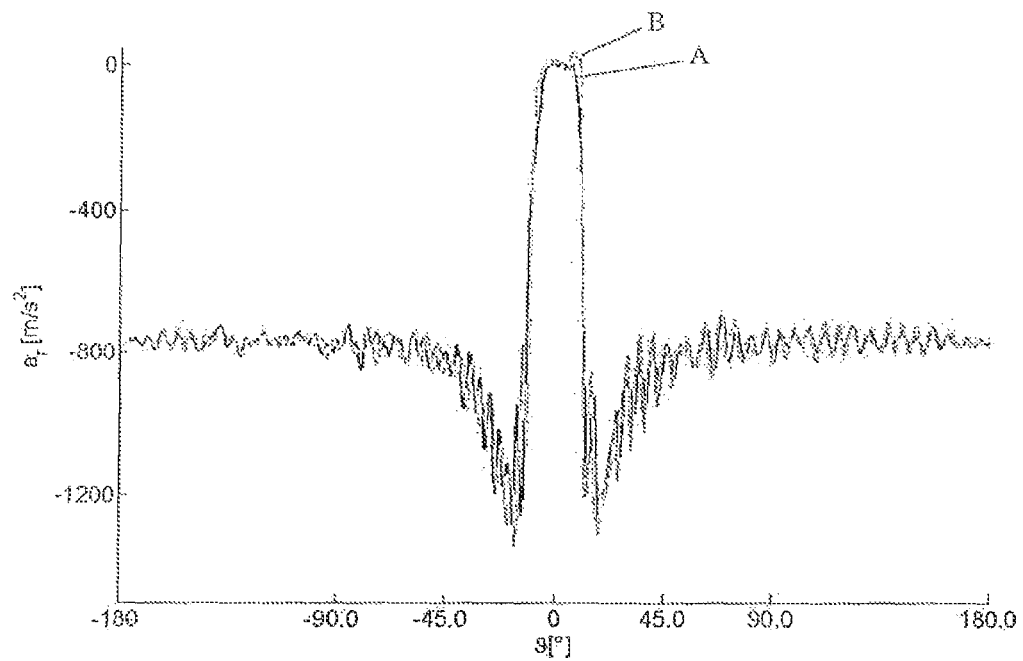
FIG. 3 shows the curves representative of the acceleration radial component measured during a revolution of the tyre by an accelerometer mounted at the centre of an inner liner of a tyre as a function of the angular position of the accelerometer relative to the centre of the footprint, the two curves being obtained for two different rolling surfaces: dry asphalt (curve A) and wet granite (curve B)
Figure 4:
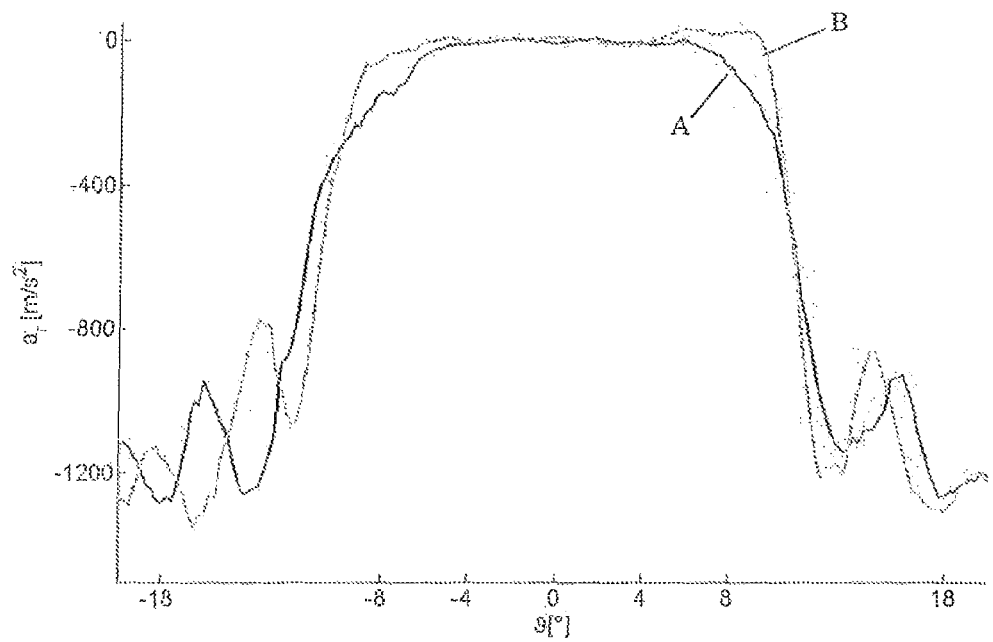
FIG. 4 shows an enlarged view of FIG. 3 around two transition regions of the two curves.

This is shown, for example, in FIG. 3, and in particular in the enlargement of FIG. 4, which show two curves of acceleration radial component obtained for two different rolling surfaces: dry asphalt (curve A) and wet granite (curve B). In particular, the curves show the acceleration radial component measured by an accelerometer mounted at the centre of the inner liner of a tyre, or more specifically a PIRELLI P6 CINTURATO™ 205/55 R16 tyre, mounted on the front right wheel of a FIAT STILO™ automobile travelling in a straight line at a speed of 60 km/h.

Each curve shows values averaged out of a plurality of tyre revolutions.

In the transition regions, at the entry and at the exit from the footprint wherein the acceleration radial component changes, in absolute value, from a maximum value to a value of nearly zero and from a value of nearly zero to a maximum value, curve B (representative of a situation of lower friction due to the rolling surface consisting of wet granite) has a much higher steepness of transition than curve A (representative of a situation of higher friction due to the rolling surface consisting of dry asphalt).

Based on this observation, the potential friction of a tyre-rolling surface system may be determined: rotating the tyre on the rolling surface so as to subject a crown portion of the tyre to an acceleration radial component; obtaining data representative of at least one of the two transition regions of the acceleration radial component the crown portion is subject to during at least one tyre revolution; processing the data obtained so as to obtain information correlated with the steepness of transition of said at least one transition region; and estimating the potential friction on the basis of the information thus obtained.

According to what defined above, the transition region corresponds to a region $R_{drop}$, or to a portion of region $R_{drop}$ contiguous to $R_{in}$, optionally combined with at least one portion of $R_{in}$ contiguous to such region $R_{drop}$.

In particular, at the entry of the crown portion of the tyre into the footprint, the transition region may have an angular extension given by $\{(\theta_{IN1} \leq \theta) \cap (\theta \leq \theta_{IN2})\}$ where θ indicates the angular position of the crown portion during one tyre revolution relative to the centre of the footprint.

For example, $\theta_{IN1}$ may be defined as:

$$\theta_{IN1} = \{\theta : (\theta < 0) \cap (a_r(\theta_{IN1}) = a_r^{threshold})\}$$

where, if the acceleration signal is sampled, the equality symbol indicates the value of the acceleration radial component lower (in absolute value) than the threshold, closer to the threshold, and where $a_r$ represents the acceleration radial component and $a_r^{threshold}$ is a predetermined threshold value. For example, $a_r^{threshold}$ may be selected according to the maximum $M_{in}$ (in absolute value) reached by the acceleration radial component at the entry into the footprint. For example $|a_r^{threshold}| = k M_{in}$, with $k \leq 1$, preferably, $k \leq 0.5$. Advantageously, $k \geq 0.2$.

According to another example, $a_r^{threshold}$ may be selected based on the acceleration radial component away from the footprint (which is about equal to the centrifugal acceleration $\omega^2_0 r_0$ of the tyre). For example $|a_r^{threshold}| = k \omega_0^2 r_0$, with $k \leq 1$, preferably, $k < 1$. Advantageously, $k \geq 0.2$, preferably $k \geq 0.5$.

According to a variant, a fixed threshold may be used. For example, a threshold may be used corresponding to a not too high value of acceleration radial component such as for example, $|a_r^{threshold}| = 50$ g, where g is the gravity acceleration.

In turn, $\theta_{IN2}$ may be any angle within or at one end of $R_{in}$, where the two angles at the two ends of $R_{in}$ are the angles where the acceleration radial component respectively is (in absolute value) for the first and the last time below an almost zero threshold of acceleration radial component (for example less than 30 g, preferably 10 g).

Preferably, $\theta_{IN2} \leq 0$. Even more preferably, $\theta_{IN2} < 0$.

In turn, at the exit of the crown portion of the tyre from the footprint, the transition region may have an angular extension given by:

$$\{(\theta_{OUT2} \leq \theta) \cup (\theta \leq \theta_{OUT1})\}$$

where $\theta_{OUT1}$ may be defined as:

$$\theta_{OUT1} = \{\theta : (\theta > 0) \cup (a_r(\theta_{OUT1}) = a_r^{threshold})\}$$

where, if the acceleration signal is sampled, the equality symbol indicates the value of the acceleration radial component lower (in absolute value) than the threshold, closer to the threshold, and where $a_r$ represents the acceleration radial component and $a_r^{threshold}$ is a predetermined threshold value. For example, $a_r^{threshold}$ may be selected according to the maximum $M_{out}$ (in absolute value) reached by the acceleration radial component at the exit from the footprint. For example $|a_r^{threshold}|=kM_{out}$, with $k\leq 1$, preferably, $k\leq 0.5$. Advantageously, $k\geq 0.2$.

According to another example, $a_r^{threshold}$ may be selected based on the acceleration radial component away from the footprint (which is about equal to the centrifugal acceleration $\omega_0^2 r_0$ of the tyre). For example $|a_r^{threshold}|=k\omega_0^2 r_0$, with $k\leq 1$, preferably, $k<1$. Advantageously, $k\geq 0.2$, preferably $k\geq 0.5$.

According to a variant, a fixed threshold may be used. For example, a fixed threshold may be used corresponding to a not too high value of acceleration radial component such as for example, $|a_r^{threshold}|=50$ g.

In turn, $\theta_{OUT2}$ may be any angle within $R_{in}$ or at one end of $R_{in}$ where the two angles at the two ends of $R_{in}$ are the angles where the acceleration radial component respectively is (in absolute value) for the first and the last time below an almost zero threshold of acceleration radial component (for example less than 30 g, preferably 10 g).

Preferably, $\theta_{OUT2}\geq 0$. Even more preferably, $\theta_{OUT2}<0$.

Figure 5:
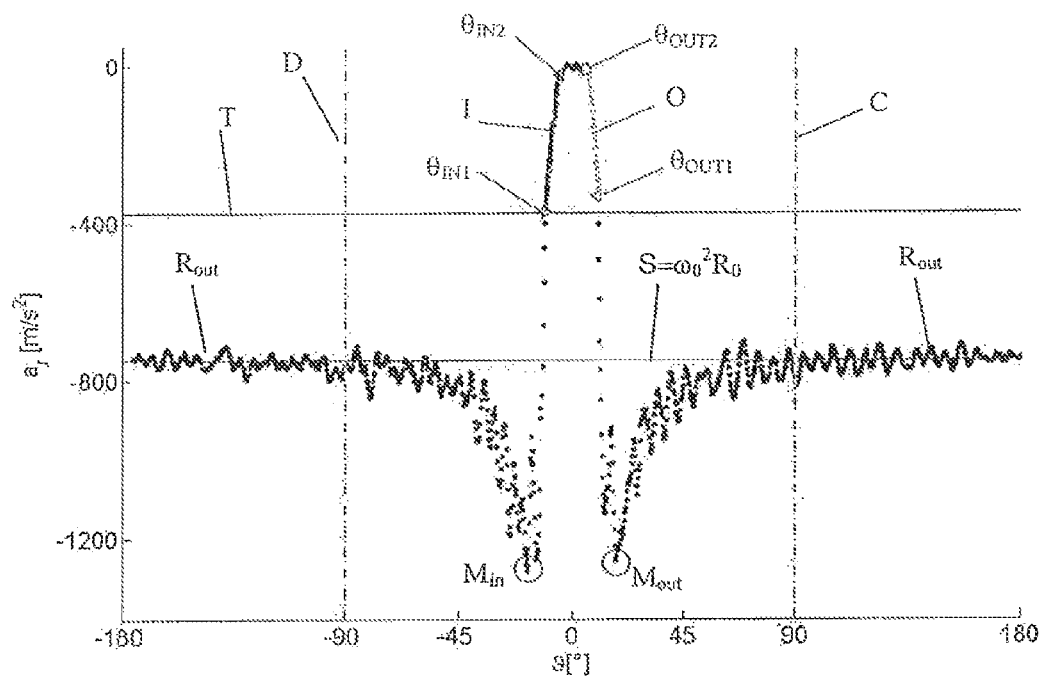
FIG. 5 schematically shows a curve representative of an acceleration radial component wherein some parameters used in the present description are highlighted.

By way of an example, FIG. 5 illustrates the concept of threshold acceleration $a_r^{threshold}$ and transition region at the entry and exit from the footprint, the centrifugal acceleration $\omega_0^2 r_0$ of the tyre, regions $R_{out}$, and the maximum $M_{in}$ e $M_{out}$ at the entry and exit from the footprint.

In particular, line I represents an example of transition region at the entry of the footprint, line O represents an example of transition region at the exit from the footprint, line T represents an exemplary threshold acceleration value with $|a_r^{threshold}|=0.5\omega_0^2 r_0$, line S indicates the centrifugal acceleration $\omega_0^2 r_0$ of the tyre, lines C and D respectively indicate the start and end angles of regions $R_{out}$, and the two circles $M_{in}$ and $M_{out}$ indicate the maximum, in absolute value, respectively at the entry and at the exit from the footprint.

In a preferred embodiment of the invention, the acceleration radial component the crown portion of the tyre is subject to is measured by an accelerometer fixed on said crown portion (for convenience, preferably on the radially inner surface of the crown portion).

Figure 9:
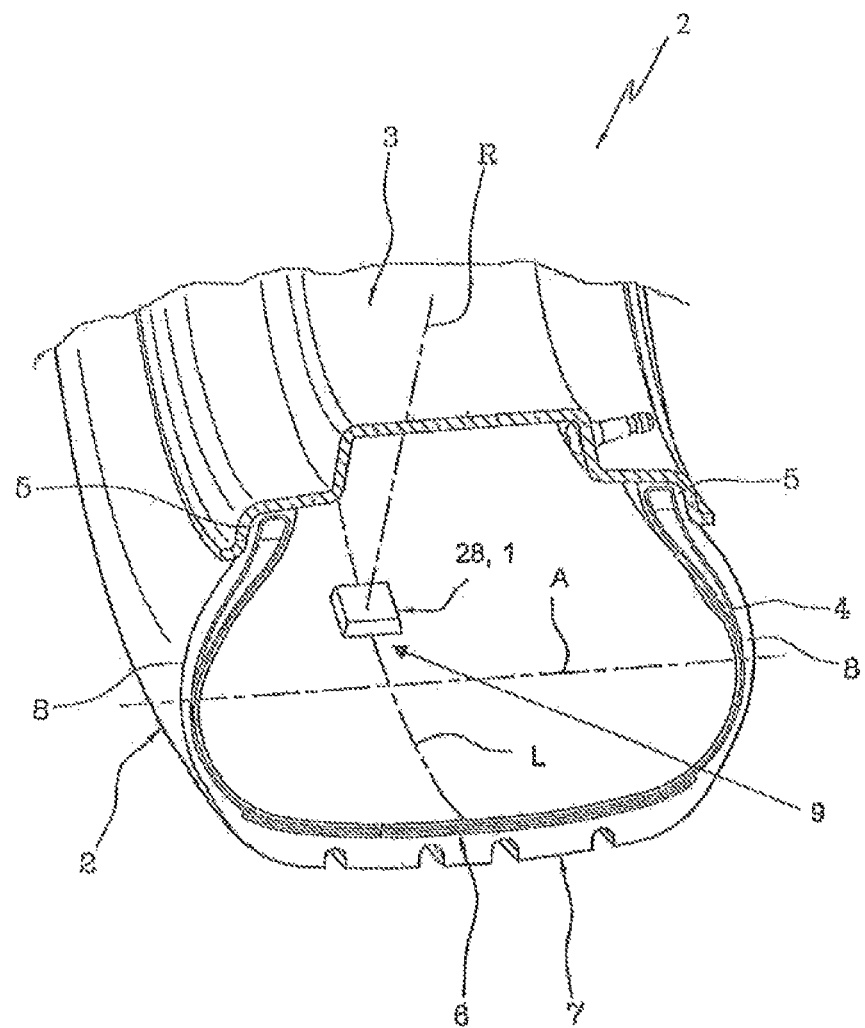
FIG. 9 schematically shows a portion of tyre comprising a monitoring device.

FIG. 9 shows a tyre 2 comprising a monitoring device 28 comprising an accelerometer 1.

In FIG. 9, letters "R", "L" and "A" respectively indicate a radial direction, a longitudinal direction (also called tangential) and a lateral direction (also called axial) of the tyre.

Tyre 2 is mounted on a rim 3. It may be mounted on any type of vehicles such as cars, vehicles for transporting goods, such as articulated lorries or trucks, motor vehicles, etc.

Tyre 2 is preferably designed to be used on vehicles provided with electronic devices installed on board suitable for cooperating and interacting with the monitoring device 28.

Tyre 2 comprises a carcass structure 4 which exhibits at least one carcass ply, not shown in detail, shaped according to a substantially toroidal configuration and engaged, through the opposite circumferential edges thereof, with two annular anchoring structures (usually identified by the name "bead wires"), each of which is located in a region 5 usually identified by the name "bead". The two annular anchoring structures are mutually spaced along a lateral direction "A" of tyre 2, parallel to the geometrical rolling axis of the tyre 2 itself.

A belt structure 6 comprising one or more belt strips is applied on the carcass structure 4 in a circumferentially outer position.

The belt structure 6 is overlapped, at an external circumferential position, by a tread band 7 on which longitudinal and transversal recesses are typically formed, arranged to define a desired tread pattern.

Tyre 2 also comprises a pair of so-called sidewalls 8 applied laterally on opposite sides on the carcass structure 4.

Reference numeral 9 indicates a crown portion of tyre 2 which extends between sidewalls 8, according to a lateral direction of the tyre.

The crown portion 9 is typically coated on the inner walls thereof with a sealing layer, or so-called "liner", comprising one or more layers of elastomeric material that is impermeable to air, adapted to ensure the hermetic seal of the tyre itself Advantageously, as shown in FIG. 9, the monitoring device 28 and accelerometer 1 are fixed at a crown portion 9, on the liner of tyre 2, by an appropriate fixing element (not shown). Preferably, accelerometer 1 is arranged substantially at the equatorial plane of tyre 2.

The fixing element is advantageously adapted to conform to the deformations undergone by the tyre structure during the rolling, in order to maintain the fixing of the monitoring device 28 to the liner stable over time.

Advantageously, besides accelerometer 1, the monitoring device 28 also comprises a radio-frequency transmitter (not shown). The monitoring device 28 may also comprise other sensors (not shown) suitable for measuring physical quantities of interest of the tyre (e.g., pressure and temperature). The radio-frequency transmitter is suitable for transmitting, through an antenna (not shown), data relating to the physical quantities measured, to a receiver (not shown) external to tyre 2. The receiver may be located on the vehicle whereon the tyre is mounted and/or outside the vehicle (for example, at a central unit, such as a central unit for gathering and processing data relating to multiple vehicles for a traffic monitoring and control system).

In particular, the data coming from accelerometer 1 are advantageously processed (optionally with an initial filtering and/or conversion to digital format) by at least one processing unit, which may be comprised in the monitoring device 28 and/or in the receiver external to tyre 2, so as to determine the potential friction between the tyre and the surface whereon the tyre rotates.

Said at least one processing unit comprises hardware and/or software modules adapted to implement the potential friction calculation algorithm. The estimated potential friction values may optionally be transmitted to systems for the active control of a vehicle dynamics or driver assistance systems (Advanced Driver Assistance Systems, or ADAS).

According to an embodiment of the invention, data processing may be performed by a fitting procedure according to which, revolution after revolution, the values of the parameters of a predetermined fitting function are determined (for example by implementing a least squares algorithm) which allow to better approximate, by means of such fitting function, the data representative of at least one transition region of the acceleration radial component measured by the accelerometer.

For example, the fitting procedure may use a parametric function of a variable x of the type:

$$f=f(x|p_1 \ldots p_n)$$

where x may, for example, represent the angular position $\theta$ of accelerometer 1 (or the time) during a complete tyre revolution and $p_1 \ldots p_n$ are parameters of which at least one is indicative of the steepness of transition of at least one transition region of the acceleration radial component.

In particular, based on the Applicant's observation that the transition regions of the acceleration radial component have a much more rounded shape the higher the potential friction between the tyre and the rolling surface, and a much more step-wise shape the lower the potential friction between the tyre and the rolling surface, the fitting function advantageously is a parametric function that has at least one parameter $p_i$ correlated with the steepness of transition (i.e. with the step-wise shape or roundness) of such transition regions.

Examples of fitting functions suitable for fitting the data representative of at least one transition region of the acceleration radial component measured by the accelerometer are the following:

$$a_r^{fit} = f_1(\theta | p_1, p_2) = p_1 e^{p_2 \theta}$$

$$a_r^{fit} = f_1(\theta | p_1, p_2) = 1 - e^{p_1 \theta^{p_2}}$$

$$a_r^{fit} = f_1(\theta | p_1, p_2) = p_1 \theta^{p_2}$$

In such examples, the parameter correlated with the steepness of transition (step shape) of the transition regions is $p_2$. In fact, more or less high values of $p_2$ correspond to more or less high steepness of transition (more or less step-wise curve) of the transition regions.

Figure 8:
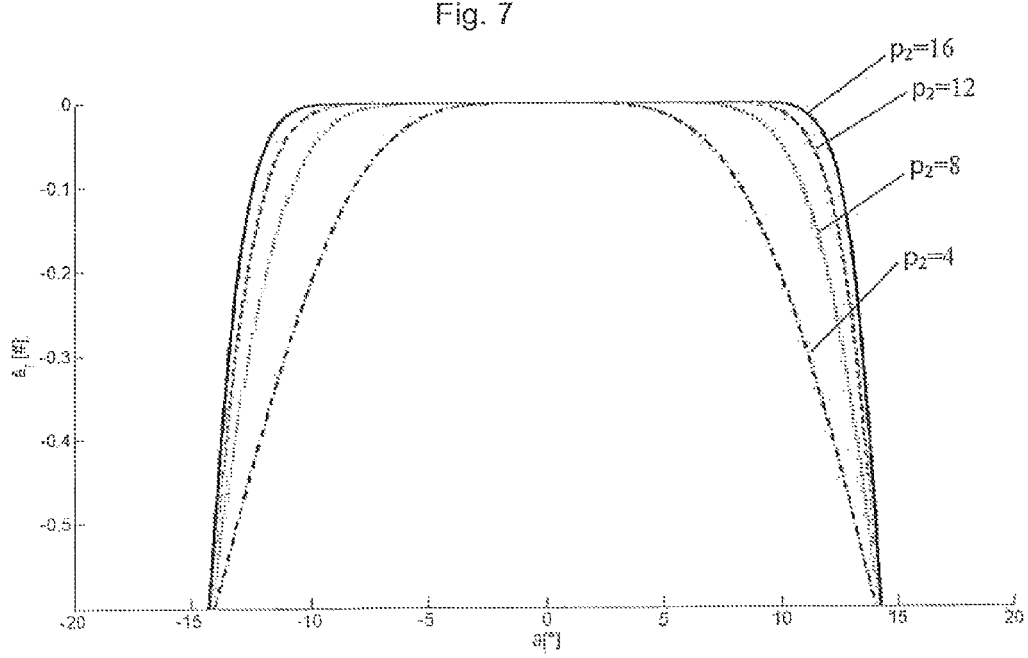
FIG. 8 shows four curves representative of a same fit function, obtained for four different values of a parameter p2 indicative of the steepness of transition of the curve transition regions.

FIG. 8 shows an example of the fitting function $a_r^{fit} = f(\theta | p_1, p_2) = 1 - e^{p_1 \theta^{p_2}}$ for four different values (4, 8, 12 and 16) of parameter $p_2$ and for $p_1 = 1$. Such figure confirms that as $p_2$ increases, the steepness of transition (step shape) of the transition region becomes increasingly higher (emphasized).

In the various examples of fitting functions, once the values of parameters $p_i$, which allow to better approximate the data representative of at least one transition region of the acceleration radial component measured by the accelerometer, have been determined, the potential friction may then be estimated based on the value determined for the parameter(s) (e.g., $p_2$) correlated with the steepness of transition of the transition region.

For example, the potential friction may be determined by comparing the value of said parameter(s) with predetermined known reference values, corresponding to predetermined potential friction values.

Alternatively, the potential friction may be obtained from said parameter(s) by applying a specific analytical function that correlates such parameter(s) with the potential friction. For example, such function may be of the type:

$$\mu_p = f(p_2 | c_1 \ldots c_m)$$

where $\theta_p$ represents the potential friction, $p_2$ the parameter correlated therewith, and $c_1 \ldots c_m$ are coefficients that are selected so as to better reproduce the known reference values.

When the fitting procedure is to be applied to both transition regions, the fitting procedure may advantageously be applied separately for the two transition regions so as to take into account any asymmetries of the curve of the acceleration radial component.

According to an alternative embodiment of the invention, the estimate of the potential friction may be performed through a similarity procedure which is based on the identification of a curve that best approximates the data representative of at least one transition region of the acceleration radial component measured by the accelerometer, among a plurality of pre-stored curves representative of different values or classes of potential friction values.

For example, the similarity procedure may comprise the following steps:
1) constructing a set of reference curves representative of different values or classes of potential friction values (for example by averaging out experimental data relating to known conditions of tyre-road interaction);
2) defining a similarity criterion which allows determining, among the pre-stored reference curves, the one that best approximates the data representative of at least one transition region of the acceleration radial component measured by the accelerometer;
3) applying the similarity criterion so as to select one of the pre-stored reference curves;
4) identifying the value or class of potential friction values associated with the selected reference curve.

In step 2), as a criterion of similarity it is possible to use, for example, the operation of correlation between real time acquired experimental data $a_r(t_i)$ and the reference curves sampled at instants $t_i$, with $i=1 \ldots n$ relating to a given tyre revolution.

In step 1), besides from averages of experimental data, the reference curves may be obtained with different mathematical models, such as exponential functions or power laws, suitably parameterized.

This similarity procedure may require lower computational effort than the fitting procedure described above. For this reason, the similarity procedure may be more suitable for being carried out by a data processing unit located within the monitoring device 28 mounted on the tyre.

In a preferred embodiment, before applying the fitting or similarity procedure, the data representative of at least one transition region of the acceleration radial component measured by accelerometer 1 may be normalized according to a normalization procedure.

Considering that the acceleration radial component $a_r$ is typically linked to the electrical signal provided by accelerometer 1 (for example, voltage V) by means of a relation of the type:

$$a_r = GV + V_{offset}$$

where G is the gain and $V_{offset}$ the offset, the normalization may advantageously be carried out so as to make the values of the acceleration radial component independent of the offset (by a subtraction operation) and of the gain (by a division operation) of the accelerometer 1.

This is highly advantageous as it prevents having to perform time-consuming calibration operations on accelerometer 1.

For example, the normalization may be carried out according to a relation of the type:

$$\tilde{a}_r(\vartheta) = \tilde{V}_r(\vartheta) = \frac{V(\vartheta) - V_0}{V_1 - V_0}$$

where $\theta$ represents the angular position of accelerometer in a complete tyre revolution, $\tilde{a}_r(\theta)$ and $\tilde{V}_r(\theta)$ represent the acceleration and voltage value normalized at an angle $\theta$, V represents the voltage in output from the accelerometer, $V(\theta)$ represents the voltage at angle $\theta$, $V_o$ and $V_1$ represent two voltage reference values.

Two normalization schemes are illustrated below by way of an example.

First Normalization Scheme

According to a first scheme, the normalization may be carried out according to a relation of the type:

$$\tilde{a}_r(\vartheta) = \frac{V_r(\vartheta) - \langle V_r(\vartheta) \rangle_{R_{in}}}{\langle V_r(\vartheta) \rangle_{R_{out}} - \langle V_r(\vartheta) \rangle_{R_{in}}} = \frac{a_r(\vartheta) - \langle a_r(\vartheta) \rangle_{R_{in}}}{\langle a_r(\vartheta) \rangle_{R_{out}} - \langle a_r(\vartheta) \rangle_{R_{in}}}$$

where $\langle V_r(\theta) \rangle_{R_{in}}$, $\langle V_r(\theta) \rangle_{R_{out}}$, $\langle a_r(\theta) \rangle_{R_{in}}$ and $\langle a_r(\theta) \rangle_{R_{out}}$ indicate respectively, the average voltage value in output from the accelerometer at the regions $R_{in}$ and $R_{out}$ and the average value of acceleration radial component in regions $R_{in}$ and $R_{out}$.

Figure 6:
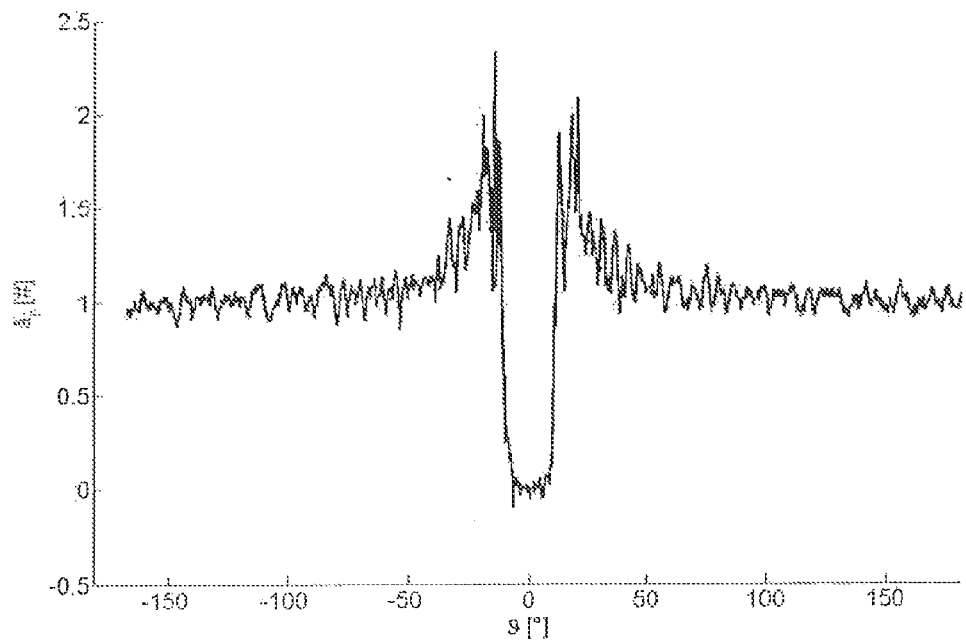
FIG. 6 shows a first example of curve representative of a normalized acceleration radial component.

FIG. 6 shows an example of curve of the acceleration radial component measured by an accelerometer placed on the inner liner of a tyre, normalized by this relation. As may be seen, with this normalization scheme the value of the normalized acceleration radial component is substantially equal to 1 in region $R_{out}$ and substantially equal to zero in region $R_{in}$.

It is noted that this normalization scheme I provides a division operation for an acceleration radial component value in region $R_{out}$ that is substantially equal to the centrifugal acceleration $\omega_0^2 r_0$ of the tyre (where $\omega_0$ and $r_0$ are the angular velocity and the radius of the tyre). Therefore, in addition to being advantageous in terms of saving calibration time and cost, this normalization scheme also allows making the normalized acceleration value $\tilde{a}_r(\theta)$ almost independent of the angular velocity $\omega_0$ of the tyre. This is extremely advantageous as it allows making also parameters $p_i$ of the fitting function $f(\theta|p_1 \ldots p_n)$ used in the fitting procedure and the (normalized) curves used in the similarity procedure independent of the angular velocity $\omega_0$ of the tyre.

Second Normalization Scheme

According to a second scheme, the normalization may be carried out according to a relation of the type:

$$\tilde{a}_r(\vartheta) = \frac{V_r(\vartheta) - \langle V_r(\vartheta)\rangle_{R_{out}}}{\langle V_r(\vartheta)\rangle_{R_{in}} - \langle V_r(\vartheta)\rangle_{R_{out}}} = \frac{a_r(\vartheta) - \langle a_r(\vartheta)\rangle_{R_{out}}}{\langle a_r(\vartheta)\rangle_{R_{in}} - \langle a_r(\vartheta)\rangle_{R_{out}}}$$

where $\langle V_r(\theta)\rangle_{R_{in}}$, $\langle V_r(\theta)\rangle_{R_{out}}$, $\langle a_r(\theta)\rangle_{R_{in}}$ and $\langle a_r(\theta)\rangle_{R_{out}}$ indicate the average voltage and acceleration radial component value, respectively, in regions $R_{in}$ and $R_{out}$.

Figure 7:
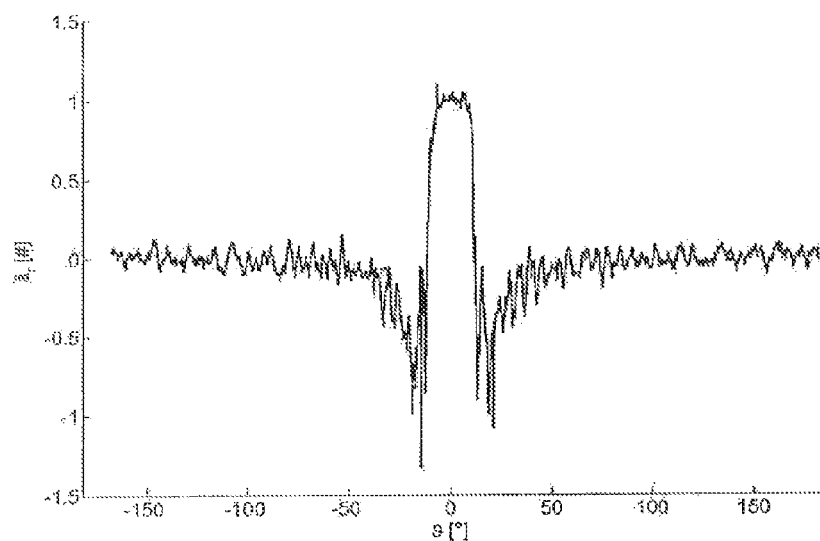
FIG. 7 shows a second example of curve representative of a normalized acceleration radial component.

FIG. 7 shows an example of curve of the acceleration radial component measured by an accelerometer placed on the inner liner of a tyre, normalized by this relation. As may be seen, with this normalization scheme the value of the normalized acceleration radial component is substantially equal to 0 in region $R_{out}$ and substantially equal to 1 in region $R_{in}$.

It is noted that also the normalization scheme II provides a division operation for an acceleration radial component value in region $R_{out}$ that is substantially equal to the centrifugal acceleration $\omega_0^2 r_0$ of the tyre (where $\omega_0$ is the angular velocity of the tyre). Therefore, besides being advantageous in terms of saving calibration time and cost, also this normalization scheme allows making the normalized acceleration value $\tilde{a}_r(\theta)$ almost independent of the angular velocity $\omega_0$ of the tyre.

This is extremely advantageous as it allows making also parameters $p_i$ of the fitting function $f(\theta|p_1 \ldots p_n)$ used in the fitting procedure and the (normalized) curves used in the similarity procedure independent of the angular velocity $\omega_0$ of the tyre.

In a preferred embodiment, the normalization procedure (e.g. according to one of the two schemes I and II mentioned above) may also be performed using variable $\theta$ normalized relative to a reference value $\theta_0$, that is with a variable $\bar{\theta}=\theta/\theta_0$. For example, $\theta_0$ may be set equal to $\theta_{IN1}$ or $\theta_{OUT1}$. The Applicant has, in fact, observed that the extension of region $R_{in}$ (and thus also the absolute value of $\theta_{IN1}$, $\theta_{OUT1}$) increases as the vertical load on the tyre increases and the inflation pressure of the tyre decreases. This type of normalization therefore has the advantage of making the normalized acceleration value $\tilde{a}_r(\theta/\theta_0)$ in a first approximation independent of the vertical load and approximately also of the inflation pressure of the tyre. This is extremely advantageous as it allows making also parameters $p_i$ of the fitting function $f(\theta/\theta_0|p_1 \ldots p_n)$ used in the fitting procedure and the (normalized) curves used in the similarity procedure in a first approximation independent of the vertical load and approximately also of the inflation pressure of the tyre.

In view of the above, in a practical embodiment of the invention, the voltage signal provided in output from accelerometer 1 mounted on the inner liner 1 of tyre 2 of FIG. 9 may be converted in the monitoring device 28 in digital format and the digital data may be sent to an external processing unit comprised in the receiver on board of the vehicle, through the radio-frequency transmitter of the monitoring device 28.

For example, revolution after revolution, such processing unit shall be adapted to process data representative of the acceleration radial component measured by accelerometer 1 at discrete values of angles $\theta i$, for $-180° \leq \theta i \leq 180°$ (or for a lower angular portion, for example between $-120°$ and $120°$).

In particular, the processing unit shall be adapted to:
- receive the data coming from accelerometer 1 of the monitoring device 28;
- starting from the data received, select data representative of at least one transition region (preferably at least that at the exit from the footprint) of the acceleration radial component;
- optionally identify regions $R_{out}$ and $R_{in}$ of the acceleration radial component and normalize the selected data using one of the normalization schemes I and II mentioned above;
- process the selected data (optionally normalized) by means of one between the fitting and similarity procedures described above so as to obtain information correlated with the steepness of transition of said at least one transition region;
- estimate the potential friction based on said information (i.e., based on the value of parameter $p_i$ correlated with the potential friction obtained with the fitting procedure, or based on the pre-stored reference curve, identified with the similarity procedure).

It is noted that if no normalization procedure is carried out (which requires processing of the data representative of regions $R_{in}$ and $R_{out}$), the analysis may be restricted to only data representative of the considered transition region. This may, for example, be advantageous because it allows using accelerometers with a limited output dynamic and/or reducing the data flow transmitted by the monitoring device 28 to the external processing unit, and thus the power consumption of the monitoring device 28.

It is further noted that the processing unit located outside the tyre allows limiting overall dimensions, weight, complexity, power consumption and cost of the monitoring device 28 positioned directly on the tyre. As described above, however, the invention also comprises the case of processing unit positioned (at least partially) within the monitoring device 28 mounted on the tyre.

The invention, enabling to make a potential friction real time estimate of a tyre-rolling surface system, may be important for enabling the development of systems for the active control of a vehicle dynamics or for driver assistance systems (Advanced Driver Assistance Systems, or ADAS). Examples of such applications are: Antilock Braking System—Braking distance improvement on slippery road; Electronic Stability Program—stability performance improvement while turning on critical manoeuvres; systems for controlling the speed and the distance from the preceding vehicle relative to the potential friction, and the like.

As already mentioned above, the method and the system according to the invention are advantageously capable of estimating the potential friction in free rolling conditions. The method and the system according to the invention in any case also operate in different conditions, as in normal driving conditions wherein the rolling of the tyre under the vehicle may be subject to slowing down, acceleration and/or bends.

In order to evaluate the performance of the invention, the Applicant has carried out experimental tests wherein potential friction values were estimated according to the invention.

In particular, the Applicant has used the normalization scheme II described above and the following fitting function in order to approximate the normalized data:

$$\tilde{a}_r^{fit} = f_1(\theta|p_1,p_2) = e^{p_1 \theta^{p_2}}.$$

The fitting procedure was applied in a transition region at the exit from the footprint with $\theta_{OUT2}=0$ and $\theta_{OUT1}=\{\tilde{a}_r^{fit}(\theta_{OUT1})\}=0.5$.

Once identified (by implementing a least squares algorithm) values of $p_1$ and $p_2$ that allowed to best approximate the data representative of such a transition region of the acceleration radial component measured in real time by the accelerometer, the Applicant has found that the potential friction could be obtained from parameter $p_2$ using a simple linear function of the type:

$$\mu_p = f_2(p_2|c_1,c_2) = c_1 + c_2 p_2$$

where coefficients $c_1$ and $c_2$ were selected to best reproduce known reference values. Considering that increasing values of parameter $p_2$ correspond to decreasing values of the potential friction $\mu_p$, coefficient $c_2$ has a negative value.

Figure 10:
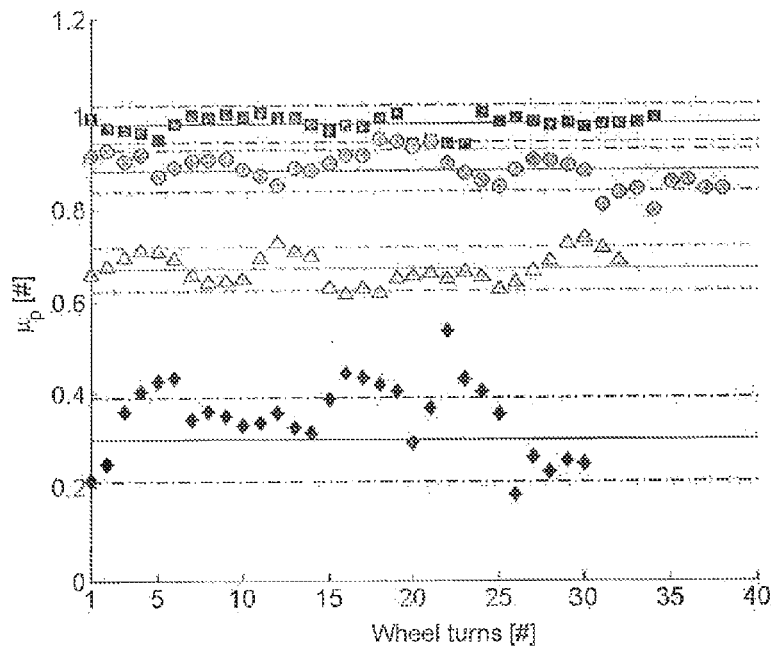
FIGS. 10-12 show the results of experimental tests carried out by the Applicant for evaluating the performance of the method and system of the invention.

FIG. 10 shows the values of potential friction $\mu_p$ obtained with a tyre, or more specifically a PIRELLI P6 CINTURATO™ 205/55 R16 tyre, mounted on the front right wheel of a FIAT STILO™ automobile travelling in a straight line at a speed of 60 km/h in conditions of free rollowing, on different rolling surfaces (diamonds in the case of wet granite, triangles in the case of dry granite, circles in the case of wet asphalt round and squares in the case of dry asphalt). In particular, each point represented in the figure represents a potential friction value estimated by averaging the data obtained over four revolutions of the tyre.

The solid line and dotted lines at the data obtained for each type of rolling surface respectively represent the mean value and the standard deviation of reference potential friction values. Such reference values were obtained by means of repeated braking tests with a dynamometric trailer (with measurement of the longitudinal force and of the vertical load) and measurement of the reference potential friction as the maximum of the ratio between longitudinal force and vertical load, as defined.

As may be noted, the potential friction values estimated according to the method of the invention well approximate the reference values.

As regards the few points outside the reference lines, they may be due to the fact that the estimated values according to the invention are punctual values obtained in different points of the rolling surface, while the reference ones are average values assumed as valid for the entire rolling surface. Therefore, we cannot exclude that the points shown in FIG. 10 outside the reference lines correspond to portions of the rolling surface wherein the real and actual potential friction differs from the average one, thereby matching that estimated according to the invention.

Figure 11:
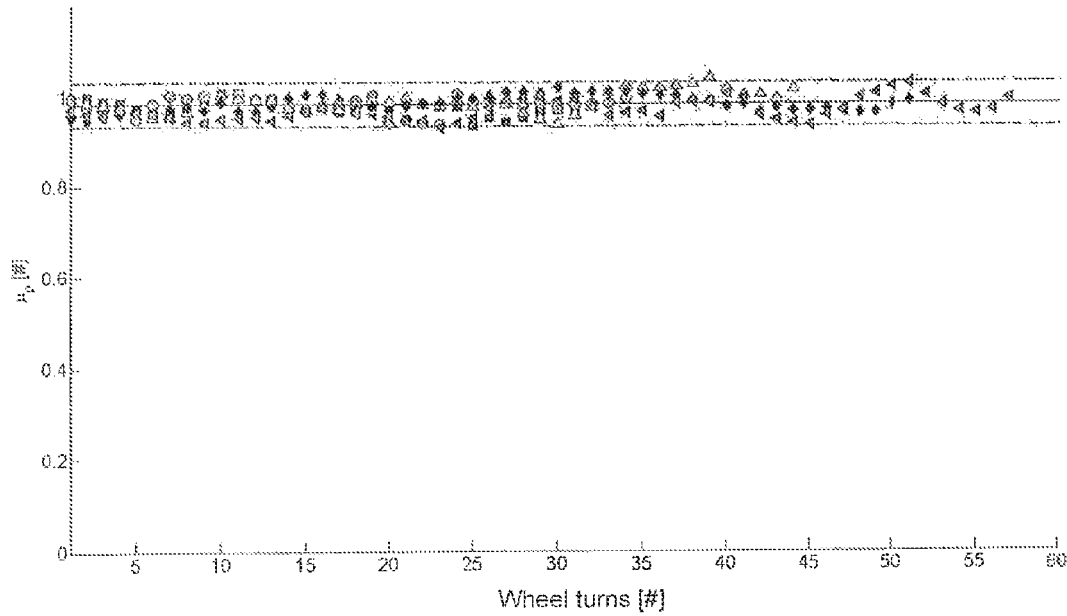

FIG. 11 shows the potential friction values $\mu_p$ obtained with a tyre, or more specifically a PIRELLI P6 CINTURATO™ 205/55 R16 tyre, mounted on the front right wheel of a FIAT STILO™ automobile travelling in a straight line under conditions of free rolling on dry asphalt, at different rolling speeds (squares in the case of 50 km/h, circles in the case of 60 km/h, upwards triangles in the case of 70 km/h, diamonds in the case of 80 km/h and leftwards triangles in the case of 120 km/h).

Figure 12:
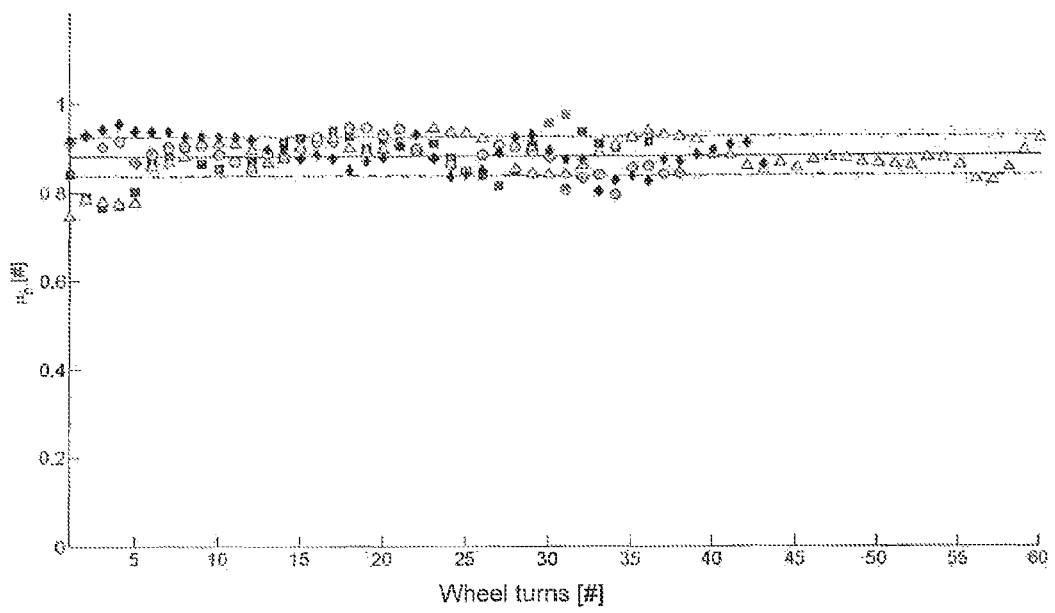

In turn, FIG. 12 shows the potential friction values $\mu_p$ obtained with a tyre, or more specifically a PIRELLI P6 CINTURATO™ 205/55 R16 tyre, mounted on the front right wheel of a FIAT STILO™ automobile travelling in a straight line under conditions of free rolling on wet asphalt, at different rolling speeds (squares in the case of 50 km/h, circles in the case of 60 km/h, upwards triangles in the case of 70 km/h, and diamonds in the case of 80 km/h).

In particular, each point represented in FIGS. 11 and 12 represents a potential friction value estimated by averaging the data obtained over four revolutions of the tyre.

FIGS. 11 and 12 show how, thanks to the normalization procedure, the potential friction values may be made almost independent of the angular velocity of the tyre.

What is claimed is:

1. A method for determining potential friction between a tyre and a rolling surface, a footprint being defined between said tyre and said rolling surface, comprising:
    rotating the tyre on the rolling surface so as to subject a crown portion of the tyre to an acceleration radial component, according to a radial direction of the tyre;
    obtaining data representative of the acceleration radial component to which said crown portion is subjected during at least one tyre revolution, said acceleration radial component comprising two regions $R_{drop}$ and a region $R_{in}$, in which said regions $R_{drop}$ represent two regions in which, due to the entry and exit of said crown portion from the footprint, the acceleration radial component respectively undergoes, in absolute value, an abrupt drop from a maximum value to a value about zero and an abrupt increase from a value about zero to a maximum value, and said region $R_{in}$ represents a region in which, due to the passage of said crown portion within the tyre footprint, the acceleration radial component is about zero;
    starting from said data, selecting data representative of at least one transition region of said acceleration radial component, said at least one transition region comprising at least one portion of one of said regions $R_{drop}$, contiguous to said region $R_{in}$;
    processing the selected data so as to obtain information correlated with the steepness of transition of said at least one transition region; and
    estimating the potential friction on the basis of said information correlated with the steepness of transition.

2. The method according to claim 1, wherein said at least one transition region also comprises at least one portion of $R_{in}$, contiguous to said at least one portion of region $R_{drop}$.

3. The method according to claim 1, wherein said at least one portion of one of said region $R_{drop}$, which is comprised in said at least one transition region, is a portion of the region $R_{drop}$, in which, due to the exit of the crown portion from the footprint, the acceleration radial component undergoes, in absolute value, an abrupt increase from a value about zero to a maximum value.

4. The method according to claim 1 wherein information correlated with the steepness of transition of said at least one transition region comprises a value of at least one transition steepness parameter, said parameter being a parameter of a parametric function adapted to approximate the data representative of said at least one transition region and being indicative of the steepness of transition of said at least one transition region.

5. The method according to claim 4, wherein the value of said at least one transition steepness parameter is obtained by determining a value of said at least one parameter that allows parametric function to best approximate said data representative of said at least one transition region.

6. The method according to claim 1, wherein the information correlated with the steepness of transition of said at least one transition region comprises a curve representative of a reference value or class of reference values of potential friction.

7. The method according to claim 6, wherein said curve representative of a reference value or class of reference values of potential friction is obtained by identifying, among a plurality of pre-stored reference curves corresponding to reference values or classes of reference values of potential friction, a curve that best approximates data representative of said at least one transition region.

8. A system for determining potential friction between a tyre and a rolling surface, a footprint being defined between said tyre and said rolling surface, comprising at least one processing unit capable of being adapted to:

obtain data representative of an acceleration radial component to which a crown portion is subjected during at least one tyre revolution, said acceleration radial component comprising two regions, $R_{drop}$, and a region $R_{in}$, in which said regions $R_{drop}$ represent two regions in which, due to the entry and exit of said crown portion from the footprint, the acceleration radial component respectively undergoes, in absolute value, an abrupt drop from a maximum value to a value about zero and an abrupt increase from a value about zero to a maximum value, and said region $R_{in}$ represents a region in which, due to passage of said crown portion within the tyre footprint, the acceleration radial component is about zero;

starting from said data, select data representative of at least one transition region of said acceleration radial component, said at least one transition region comprising at least one portion of one of said regions $R_{drop}$, contiguous to said region $R_{in}$, and process the selected data so as to obtain information correlated with steepness of transition of said at least one transition region and estimate potential friction on a basis of said information correlated with the steepness of transition.

9. The system according to claim 8, further comprising a tyre.

10. The system according to claim 9, further comprising a monitoring device operatively associated with the tyre, said monitoring device comprising an accelerometer, operatively associated with said crown portion, capable of measuring the acceleration radial component to which said crown portion is subjected during rolling of the tyre.

\* \* \* \* \*

UNITED STATES PATENT AND TRADEMARK OFFICE
CERTIFICATE OF CORRECTION

| | | |
|---|---|---|
| PATENT NO. | : 8,626,454 B2 | Page 1 of 1 |
| APPLICATION NO. | : 13/825712 | |
| DATED | : January 7, 2014 | |
| INVENTOR(S) | : Riccardo Tebano and Giorgio Audisio | |

It is certified that error appears in the above-identified patent and that said Letters Patent is hereby corrected as shown below:

Title Page, item (75) Inventors: Second Inventor's name "Glorgio Audisio", should read --Giorgio Audisio--.

Signed and Sealed this
First Day of July, 2014

Michelle K. Lee
*Deputy Director of the United States Patent and Trademark Office*